United States Patent [19]

Thyen et al.

[11] 4,424,898

[45] Jan. 10, 1984

[54] NEEDLE AND SUTURE HOLDER AND PACKAGE

[75] Inventors: Eberhard Thyen, Middlesex; Charles D. Carr, Martinsville, both of N.J.

[73] Assignee: Ethicon, Inc., Somerville, N.J.

[21] Appl. No.: 366,508

[22] Filed: Apr. 8, 1982

[51] Int. Cl.³ .............................................. A61B 17/06
[52] U.S. Cl. .................................... 206/63.3; 206/380
[58] Field of Search ...................... 206/63.3, 227, 380, 206/382, 381

[56] References Cited

U.S. PATENT DOCUMENTS

| | | | |
|---|---|---|---|
| 3,545,608 | 12/1970 | Berger | 206/63.3 |
| 3,857,484 | 12/1974 | Thyen | 206/63.3 |
| 4,135,623 | 1/1979 | Thyen | 206/63.3 |
| 4,183,431 | 1/1980 | Schmidt et al. | 206/63.3 |

*Primary Examiner*—Joseph Man-Fu Moy
*Attorney, Agent, or Firm*—Robert L. Minier

[57] ABSTRACT

A means for removably securing a plurality of needles wherein a plurality of holding means are disposed from one surface of a member, the holding means having an elongated shape with adjacent longer sides being substantially parallel. The needle is gripped on its inside curved surface in at least two points and on its outside curved surface at one point.

11 Claims, 10 Drawing Figures

NEEDLE AND SUTURE HOLDER AND PACKAGE

BACKGROUND OF THE INVENTION

This invention relates to holders for needles and more particularly to holders and packages which provide for the delivery of sutures containing attached needles.

In the packaging of surgical needles including surgical needles to which there are attached sutures, it is important that the needles be sufficiently secured that they will not be jarred or displaced during the packaging operation as well as the shipping of the package and the opening of the package in the operating arena. Jarring or displacement of these very sharp needles will often dull their cutting edges and reduce their efficiency in closing tissue very often resulting in increased trauma of the tissue. Also, it is preferred that the needles be held in a manner in which they are sufficiently separated and are readily available to the nurse or surgeon at the appropriate time. Also, suture materials, particularly monofilaments such as catgut, polydioxanone and the like, especially the heavier deniers, are known to take a set during storage; i.e., they generally retain the shape of their position in the package when removed from the package. Hence, the package should be designed so that any tight bends or curves required in order to package the suture be eliminated. Also, for economic reasons the suture package should be designed to accept various size needles and sutures.

Packages for armed sutures; i.e., sutures where the needle is attached, which provide for some degree of needle separation, are disclosed, for example, in U.S. Pat. Nos. 4,135,623; 4,034,850; and 3,857,484. These patents are representative of the many patents which show needle separation within the package. Also, packages for use with the heavier denier monofilament sutures which provide a package which substantially reduces undesirable "set" of the suture are described in U.S. Pat. No. 3,972,418.

SUMMARY OF THE PRESENT INVENTION

The present invention provides a holder for a plurality of needles in spaced apart relationship and in the same plane. The improved holder presents the needles so that they are easily accessible to the user and individual needles may be removed without disrupting the other needles in the holder. In certain embodiments of the holder of the present invention, the holder includes means for containing monofilament sutures, especially the heavier denier monofilament sutures, in a manner so that they do not take an undesirable set and still allow for the removal of single armed sutures from the holder. The holder of the present invention is economical to make and may be used with needles and sutures of various sizes.

The holder of the present invention contains a plurality of sterile, curved, surgical needles in spaced apart relationship with the needles aligned and held in substantially the same plane. The holder comprises a planar member with a plurality of holding means disposed from one surface of the planar member. Each of the holding means has an elongate shape with facing longer sides of adjacent holding means having portions substantially parallel. A curved needle is placed between the facing longer sides and is gripped on its inside curved surface or its concave surface in at least two areas or points and on its outside curved surface or its convex surface in one area or point to hold the needle in a plane parallel to the planar member.

In a preferred embodiment of the present invention, the holder is a sterile suture package for holding a plurality of sutures with attached curved needles with the needles being removably secured in spaced apart relationship in the holder and the sutures being disposed so as to allow for single strand dispensing of the sutures and substantially reduce detrimental set in the suture strand. In this embodiment, the holder comprises a pair of interlocking molded members. One of the molded members has a planar surface with a plurality of raised holding means disposed from the center portion of the planar surface. Each of the holding means has an elongate shape with facing longer sides of adjacent holding means having portions substantially parallel whereby a curved needle placed between facing longer sides is gripped on its inside curved surface at two points and on its outside curved surface at one point to hold the needle in a plane parallel to the planar member. The circumferential edge of this planar member is raised on the same side of the member as said holding means to form a horizontal ledge about the periphery of the member. The planar member also has a plurality of raised areas disposed from the same side as the holding means and ledge with said raised areas disposed in the area between the holding means and the ledge. The second molded member is also generally planar in shape with an upwardly extending ledge about its periphery. Said second planar member is co-extensive with the first planar member to provide a close fit between the upwardly extending ledge of the second member and the circumferential ledge of the first member. The second planar member has a plurality of raised areas disposed so as to be frictionally inserted within the raised areas of the first member to lock the two members together. The horizontal ledge of the first member and the circumferential edge of the second member cooperate to form a channel around the outer perimeter of the holder in which the sutures attached to the needles are disposed and held.

The holder with the needles and sutures therein is placed in a primary package. The primary package may comprise a pair of polycoated foil sheets sealed about their periphery. If desired, the package may include an appropriately designed paper member sealed between the two sheets and on top of the holder to allow for easy and simple access to the needles and sutures when desired. The primary package is preferably overwrapped with clear film on one side and polycoated foil or paper member on the opposite side with the periphery of the film and foil sealed together with a peelable seal. The overwrapped package is sterilized by techniques well known in the art. In use, the overwrap is removed to expose the sterile primary package. The sterile package is opened to expose the holder which may be removed from the package. Once the holder is removed from the primary package, the sutures may be removed from the holder simply by picking up a needle with a suitable instrument and drawing the suture through the channel around the circumference of the holder. Once removed, the suture is characterized by having only a gentle curve and no coils.

BRIEF DESCRIPTION OF THE DRAWINGS

The invention will be more fully described in conjunction with the accompany drawings wherein.

DETAILED DESCRIPTION OF THE DRAWINGS

Figure 1:
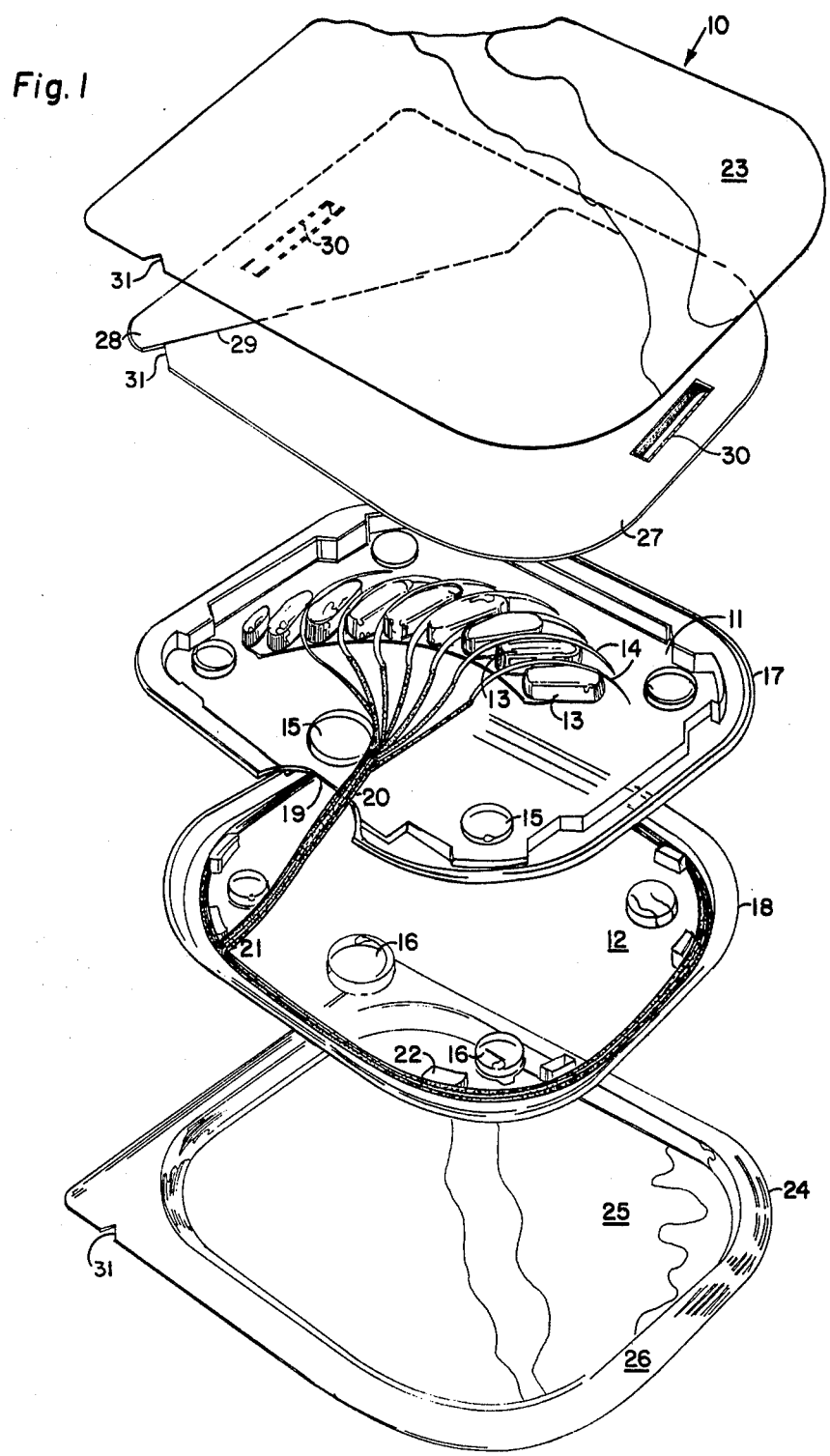
FIG. 1 is an exploded perspective view of a package for needles and sutures in accordance with the present invention showing the holder of the present invention and the various parts of the package.

In FIG. 1 there is shown an exploded view of a package 10 of the present invention showing its various portions. In this embodiment the package comprises a needle holding member and an intermeshing, interlocking filament or suture holding member 12. The needle holding member has a plurality of raised areas 13 which are spaced apart in a manner so that a needle 14 placed between the area is removably secured by the areas. The needle holding member also has a plurality of raised areas 15 for interlocking with complementary raised areas 16 in the filament holding member. The periphery 17 of the needle holding member fits into the periphery 18 of the filament holding member. There is an opening 19 disposed in the needle holding member so that the filaments or sutures 20 attached to each of the needles may pass through this opening and into a channel 21 disposed about the periphery of the interlocking members. The filaments are held in the periphery of the members by the raised separator areas 22. Also, as previously mentioned, the filament holding member has complementary raised areas 16 which fit into the raised areas 15 of the needle holding member to lock the two members together.

The needle and suture holder interlocking members are placed in a suitable primary package. In this embodiment the package comprises a pair of substantially co-extensive foil members 23 and 24. The foil members are slightly larger than the interlocking members. The foil member 24 is dished or hollowed 25 to accept the interlocking members and the foil members include a heat seal adhesive 26 about the periphery of their facing surfaces to seal the interlocking members between the foil members. The package includes a die cut paperboard member 27 which provides ready access to the needle and suture holding member when desired, as hereinafter described. The paperboard member is substantially co-extensive with the interlocking members and includes a tab 28 which may be sealed between the foil members at the periphery thereof. The paperboard member includes a diagonal die cut 29 across the width of the member. The member 27 also includes cut out areas 30 to assist in the alignment of the member in the package. The foil members as well as the paperboard member include tear notches 31 disposed adjacent the tab and die cut of the paperboard member. This configuration allows for ready access to the interlocking members as will be described in conjunction with FIGS. 7 and 8.

Figure 2:
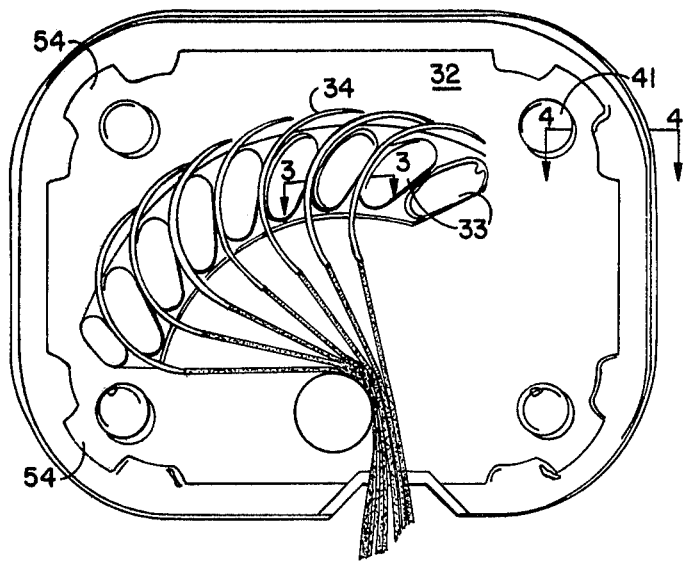
FIG. 2 is a plan view of a portion of a holder of the present invention.

As may be more clearly seen in FIG. 2, the needle holding member 32 has a plurality of spaced apart, raised, elongated areas 3. Adjacent longer sides of adjacent raised areas have portions parallel. The raised areas may be oval, elliptical, rectangular or similarly shaped.

Figure 2A:
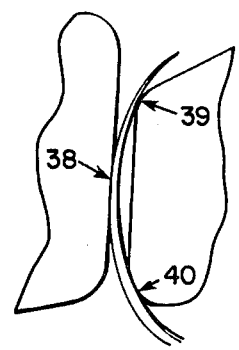
FIG. 2a is a greatly enlarged plan view of a portion of the holder of FIG. 2.
Figure 3:
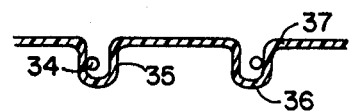
FIG. 3 is a cross-sectional view taken along line 3—3 of FIG. 2.

The spacing between raised areas should be just slightly smaller than the smallest needle curve which it is desired to be used with the holder. As may be seen in the FIGS. 2a and 3, the needle 34 fits between the raised areas and the sides 35 of the raised areas are thinner than either the bottom edge 36 or the upper edge 37 of the raised areas. This allows for flexing of the raised areas so that various sized needles may be inserted with slight force between the spaced apart areas and held firmly in place. The eliptical configuration of the raised areas causes the raised areas to contact the needle at three point. This is more clearly shown in the enlarged view depicted in FIG. 2a where the points are identified by arrows. One point 38 being on the outside curved surface of the needle and two points 39 and 40 being on the inside curved surface of the needle. This contact of the needle also allows for various sized needles to be used in the same package and provides for a positive holding of the needles in a planar configuration in the package. Our new package, in many instances, will be used with what are termed control release sutures, that is, sutures which, when a correct amount of pull is given the needle, the needle will disengage from the suture. These control release sutures are desirable so that once the doctor has closed a wound it is a simple matter to remove the needle from the suture with a slight tug. These control release sutures require a package that holds the needle and suture in place during transport, prevents damage to the cutting edge of the needle, yet allows the nurse or surgeon to remove the needle and suture from the package without separating the needle from the suture. Our improved package provides such desirable characteristics in that it holds the needle in the package in a positive and secure manner yet the needle and suture is readily accessible to the nurse or doctor and may be easily removed with little chance of separating the needle from the suture.

Figure 4:
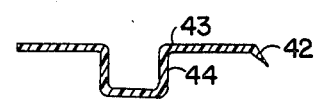
FIG. 4 is a cross-sectional view taken along line 4—4 of FIG. 2.

The needle holding member also includes a plurality of raised impressions 41 disposed between the eliptical raised areas and the outer periphery of the member for gripping the filament holding member as previously explained. As shown in FIG. 4, the outer periphery of the needle holding member ends in a downwardly curved area 42 which is meant to produce a close fit with the filament holding member. This area 42 is attached or disposed from a horizontal ledge 43 attached to the upright leg 44. This portion of the periphery cooperates with the periphery of the filament holding member to produce a channel about the periphery of the members in which the filaments or sutures are encased.

Figure 5:
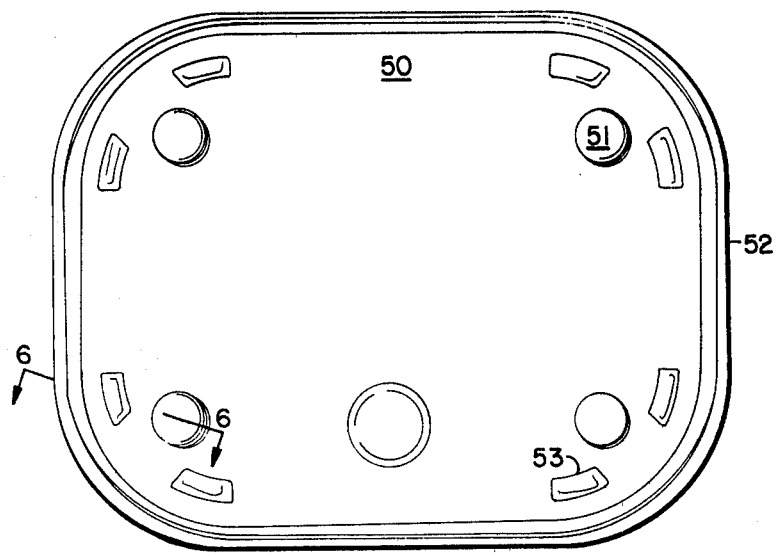
FIG. 5 is a plan view of another portion of a holder of the present invention.
Figure 6:
FIG. 6 is a cross-sectional view taken along line 6—6 of FIG. 5.

Referring to FIGS. 5 and 6, there is shown a filament holding member 50 which intermeshs and interlocks with the needle holding member. The filament holding member is substantially the same size and shape and co-extensive with the needle holding member. It includes a plurality of raised areas 51 disposed and positioned so as to fit within raised areas of the needle holding member. The filament holding member terminates about its periphery in an upwardly extending vertical wall 52. The filaments are wound about the circumference of the filament holding member and are maintained at the circumference or about the circumference by the separators 53. The separators 53 match or intermesh with the separates 54 positioned about the periphery of the needle holding member, as shown in FIG. 2, to form a channel in which the sutures are stored. These matching intermeshing separators prevent the sutures from slipping between the top and bottom holding members.

Figure 6A:
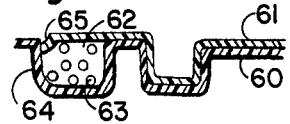
FIG. 6a is a cross-sectional view depicting the circumferential edge when the portions of the holder depicted in FIGS. 2 and 5 are interlocked to form the holder of the present invention.

In FIG. 6A, there is shown a cross-section of the outer periphery of the needle holding member and the filament holding member in place. The raised area 60 of the filament holding member fits inside the raised area 61 of the needle holding member. The outer periphery of the needle holding member and the outer periphery of the filament holding member form a channel 62 within which the suture filaments 63 lie. The side or very outer edge of this channel is formed by the upwardly extending vertical wall 64 of the filament holding member. The lip 65 at the outer periphery of the needle holding member engages the vertical wall and deflects it outwardly to hold the two members together and confine the filaments within the channel formed by the two members.

The needle holding member and the suture holding member may be formed by various techniques which are well known in the art. It is generally preferred that the members be formed with pressure or vacuum forming or other types of molding as are well known. The holding members may be made from the various materials that are thermoformable, such as the polyolefins, polyethylene, polypropylene, celluloid type materials, vinyls and the like.

The size and shape of the needle holding areas are important to the present invention. The size and shape of the needle holding areas provides that the package may be used with various sized needles. Also, the size and shape of the needle holding areas allows the various sized needles to be held in a positive manner in a planar position. As previously mentioned, the shape of the members are generally oval or eliptical and are shaped and sized so as to contact a needle at one point on the convex or outside curved surface of the needle and at two points on the convex or inside curved surface of the needle. This allows for smaller needles having tighter curves to be held by the areas as well as the larger needles which have gentler curves to be held by the same areas.

Our new package may be used with curved needles having a diameter of 10 mils or larger and comprising from about one quarter of a circle to five-eigths of a circle.

The sutures may be made from various absorbable or non-absorbable synthetic or natural materials as are well known.

Figure 7:
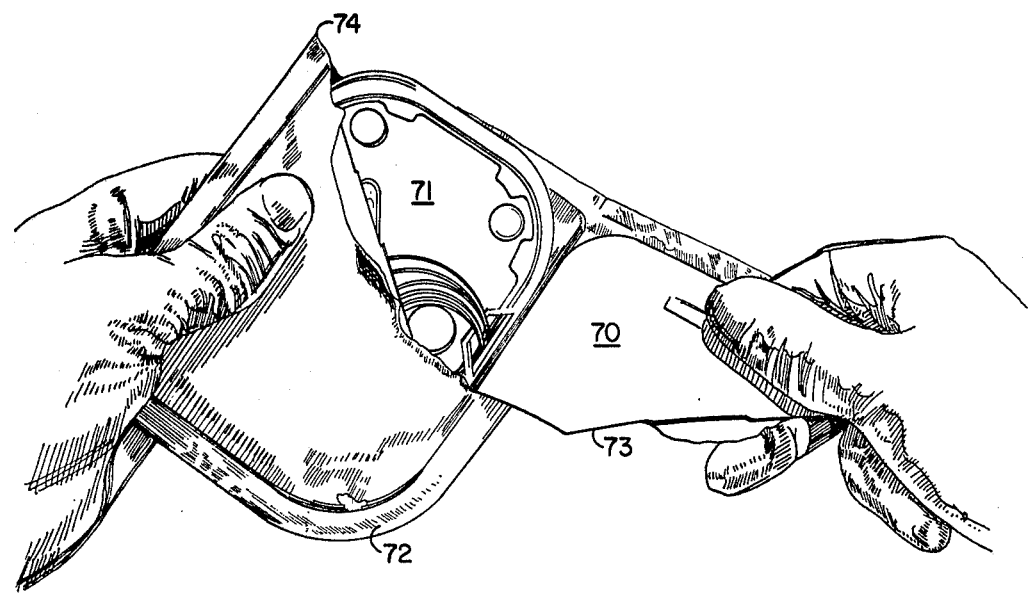
FIG. 7 is a perspective view showing a package of the present invention being initially opened in its sterile condition.
Figure 8:
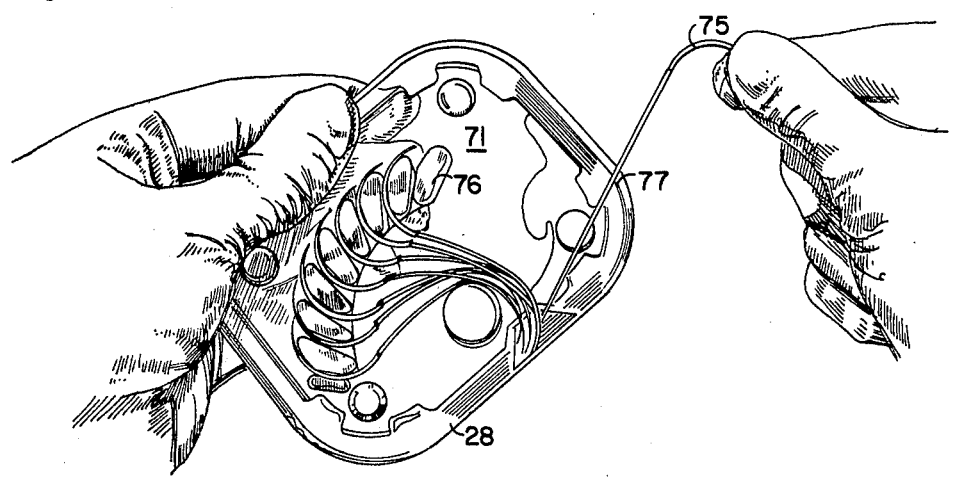
FIG. 8 is a perspective view depicting one of the needles with the attached suture being removed from a holder of the present invention.

In a preferred embodiment of the present invention, the needle and suture or filament holding members are packaged in an appropriate overwrap so that a sterile package with sterile needled sutures are presented to the nurse or surgeon for use. Referring to FIGS. 7 and 8, the sterile package comprises an appropriately designed stiff paper member 70 disposed on top of the needle holding member 71. This paper member serves to aid in the opening of the package as will be described hereinafter. The member may be made from a moisture absorbing material, such as Kraft paper, to protect hydrolyzable type sutures from being degraded by minute amounts of moisture. The paper and the needle and suture holding means 71 is totally encased in a foil laminate 72 which is heat sealed about its periphery as is well known in the art. The paper member has an outer tab which is caught in the seal of the periphery of the foil laminate. The paper includes a scored or die cut portion 73 which aids in opening of the package. The opening of the package is depicted in FIG. 7. As may be seen, the needle and suture holding member 71 is disposed within the foil laminate 72. The laminate is notched 74 and when the notch is torn the paper and laminate are torn along the score line 73 of the paper member to provide access to the needle and suture holder 71. As more clearly shown in FIG. 8, the needle and suture holder 71 has been removed from the outer wrap and it is now a simple matter for the nurse or doctor to remove a needle 75 between the raised holding means 76 and remove the suture 77 from the channel 78 of the needle and suture holder without disturbing the other needles or sutures and provides for single strand delivery of the needled suture. It is important that the sutures be wound in the configuration as shown so that when a needle and suture is removed from the holder any coiling of the suture is away from the point of the needle and does not interfere with the surgeon's use of the needle.

Having now described the invention in specific detail and exemplified the manner in which it may be carried into practice, it will be readily apparent to those skilled in the art that innumerable variations, applications, modifications, and extensions of the basic principles involved may be made without departing from its spirit or scope.

What is claimed is:

1. Means for removably securing a plurality of sterile, curved, surgical needles in spaced relationship with said needles lying and being held in substantially the same plane, said means comprising:
   a planar member, and a plurality of holding means disposed from one surface of said planar member, each of said holding means having an elongate shape, adjacent longer sides of adjacent holding means having portions parallel whereby a curved needle placed between said adjacent longer sides is gripped on its inside curved surface or its concave curved surface in at least two points and on its outside curved surface or its convex surface at one point to hold the needle in a plane parallel to said planar member.

2. Means according to claim 1 wherein the planar member and the holding means are made from a single molded sheet with the holding means disposed outwardly from the remainder of the sheet.

3. Means according to claim 1 wherein the holding means are generally oval in shape with the longer curved sides of each holding means having flattened edges and the longer curved sides of adjacent holding means being parallel.

4. Means according to claim 1 wherein there is one more holding means than needles to be held.

5. Means according to claim 4 including sutures attached to said needles.

6. A suture package for a plurality of sutures with attached needles, said needles being removably secured in said package in spaced apart relationship and said sutures being disposed within said package so as to allow single strand dispensing of a needled sutured from said package comprising:
(a) a planar member;
(b) a plurality of holding means disposed from one surface of said planar member, each of said holding means having an elongate shape, adjacent longer sides of adjacent holding means having portions parallel whereby a curved needle placed between said adjacent longer sides is gripped on its inner curved surface or concave surface in at least two areas and on its outside curved surface or convex surface in at least one area to hold the needle in a plane parallel to said planar member; and
(c) means to engage and hold the sutures attached to said needles, said means being disposed circumferentially about said plural holding means.

7. A needled suture retainer for holding a plurality of sutures with attached needles, said needles being removably secured in spaced apart relationship in said retainer and said sutures being disposed so as to allow single strand dispensing of said needled sutures, said retainer comprising:
a pair of interlocking, molded members, the first of said molded members having a planar surface including a plurality of raised holding means disposed in the center portion of said planar surface on one side thereof, each of said holding means having an elongate shape, adjacent longer sides of adjacent holding means having portions parallel whereby a curved needle positioned between said adjacent longer sides is gripped on the inside curved surface of the needle at two points and on the outside curved surface of the needle at one point to hold the needle in a plane parallel to said planar surface, the circumferential edge of said first member including a horizontal ledge extending from a vertical wall extending on the same side of the member as said holding means, said first member including a plurality of raised areas disposed from the same side of the member as said holding means and being disposed in the area between said holding means and said circumferential edge and a second molded member generally planar in shape and having a plurality of raised areas disposed so as to engage the raised areas of said first member to lock the two pieces together and the circumferential edge of said second member terminating in an upwardly extending vertical wall which engages the outer periphery of said first holding member to form a channel around said outer periphery in which the sutures attached to said needles are held and disposed.

8. A needled suture retainer according to claim 7 wherein the parallel portions of the longer sides of the holding means are thinner in the central portion thereof than at the ends.

9. A needled suture retainer according to claim 7 or 8 wherein the circumferential edge of the first holding member terminates in a downwardly extending lip configured to frictionally engage the upwardly extending vertical wall at the circumferential edge of said second holding member.

10. A suture package wherein the needled suture retainer of claim 7 or 9 is disposed between a pair of foil sheets, the periphery of said foil sheets extending beyond the outer edge of said suture retainer and being sealed together at said periphery to hermetically seal said retainer between said foil sheets.

11. A suture package according to claim 10 including a piece of Kraft paper substantially co-extensive with said retainer and being disposed between said foil sheet, said paper including a tab disposed in the area where the foil sheets are sealed and said paper including a scored portion to assist in the opening of the package and the presentation of said retainer.

* * * * *